(12) United States Patent
Debeaud et al.

(10) Patent No.: US 9,789,035 B2
(45) Date of Patent: Oct. 17, 2017

(54) LIP COMPOSITION IN THE FORM OF AN INVERSE EMULSION COMPRISING A HUMECTANT, AND TREATMENT PROCESS USING THE SAME

(71) Applicant: L'OREAL, Paris (FR)

(72) Inventors: Roshanak Debeaud, L'hay les Roses (FR); Regine Imbert, Bretigny-sur-Orge (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/102,468

(22) PCT Filed: Dec. 22, 2014

(86) PCT No.: PCT/EP2014/079073
§ 371 (c)(1),
(2) Date: Jun. 7, 2016

(87) PCT Pub. No.: WO2015/097185
PCT Pub. Date: Jul. 2, 2015

(65) Prior Publication Data
US 2016/0310374 A1 Oct. 27, 2016

(30) Foreign Application Priority Data

Dec. 23, 2013 (FR) ..................... 13 63424

(51) Int. Cl.
| | | |
|---|---|---|
| A61K 8/02 | (2006.01) | |
| A61K 8/06 | (2006.01) | |
| A61K 8/31 | (2006.01) | |
| A61K 8/34 | (2006.01) | |
| A61K 8/891 | (2006.01) | |
| A61K 8/92 | (2006.01) | |
| A61K 8/49 | (2006.01) | |
| A61K 8/58 | (2006.01) | |
| A61K 8/894 | (2006.01) | |
| A61Q 1/04 | (2006.01) | |
| A61Q 19/00 | (2006.01) | |

(52) U.S. Cl.
CPC ............... *A61K 8/064* (2013.01); *A61K 8/31* (2013.01); *A61K 8/345* (2013.01); *A61K 8/4973* (2013.01); *A61K 8/58* (2013.01); *A61K 8/585* (2013.01); *A61K 8/891* (2013.01); *A61K 8/894* (2013.01); *A61K 8/922* (2013.01); *A61Q 1/04* (2013.01); *A61Q 19/001* (2013.01); *A61Q 19/007* (2013.01); *A61K 2800/43* (2013.01); *A61K 2800/49* (2013.01); *A61K 2800/596* (2013.01); *A61Q 19/00* (2013.01)

(58) Field of Classification Search
None
See application file for complete search history.

(56) References Cited

U.S. PATENT DOCUMENTS

| | | |
|---|---|---|
| 5,389,361 A | 2/1995 | Osterried et al. |
| 5,703,041 A | 12/1997 | Afriat et al. |
| 6,426,079 B1 * | 7/2002 | Bara ............... A61K 8/064 424/401 |
| 2001/0019717 A1 | 9/2001 | Nojiri et al. |
| 2002/0018760 A1 | 2/2002 | Vatter et al. |
| 2004/0228894 A1 | 11/2004 | Nojiri et al. |
| 2010/0272766 A1 | 10/2010 | Vatter et al. |

OTHER PUBLICATIONS

International Search Report dated May 6, 2915, in PCT/EP2014/079073 filed Dec. 22, 2014.

* cited by examiner

*Primary Examiner* — Susan Tran
(74) *Attorney, Agent, or Firm* — Oblon, McClelland, Maier & Neustadt, L.L.P.

(57) ABSTRACT

The present invention relates to a cosmetic composition of water-in-oil emulsion type comprising: —from 8% to 70% by weight of an aqueous phase comprising at least one moisturizer/humectant, —from 30% to 92% by weight relative to the weight of the composition of a lipophilic phase comprising: —1% to 20% by weight relative to the weight of the composition of a polar non-volatile hydrocarbon-based first oil, a volatile or non-volatile, hydrocarbon-based or silicone apolar oil, the composition comprising at least one silicon oil; —a particular solid compound whose melting point is at least 30° C., the composition comprising not more than 20% by weight of the lipophilic phase of hydrocarbon-based apolar compound of synthetic origin, —at least one emulsifying surfactant system. the invention also relates to a lip treatment process in which the composition according to any one of the preceding claims is applied to the lips.

15 Claims, No Drawings

LIP COMPOSITION IN THE FORM OF AN INVERSE EMULSION COMPRISING A HUMECTANT, AND TREATMENT PROCESS USING THE SAME

The present invention relates to a composition for treating the lips which is in the form of an inverse emulsion comprising at least one humectant or moisturizer and a lipophilic phase comprising a nourishing oil.

The invention also relates to a lip treatment process using the said composition.

The present invention is more particularly concerned with moisturizing compositions intended to be applied to the lips, such as lip balms or sera, which may be in solid or fluid forms. Most of these compositions are anhydrous and generally comprise glycerol as moisturizer/humectant, and also a relatively large content of apolar hydrocarbon-based compounds, for instance polybutenes, polyisobutenes, which may or may not be hydrogenated, paraffins, liquid petroleum jellies, and, depending on the presentation form, variable contents of structuring agent chosen from waxes, especially apolar waxes, or pasty compounds.

Compositions also exist, to a smaller extent, comprising water, besides the abovementioned ingredients, and which are in the form of oil-in-water direct emulsions.

When these compositions are applied, they moisturize the lips, forming an occlusive barrier at their surface which contributes towards keeping water in the region of the lips. Their appearance and softness are thereby improved.

However, it has been found that the moisturizing effect was not persistent and that it decreased more or less rapidly after stopping the application of the compositions.

In addition, even though feeling the presence of the deposit of these compositions on the lips may be associated by users with a barrier action against external attack, it nevertheless remains that, in certain cases, this deposit may be perceived as being too heavy, too greasy, or even tacky.

The search consequently continues for lip treatment compositions whose effect is more persistent over time, even after stopping the application, and whose deposit is light on the lips, sparingly greasy or non-greasy, and sparingly tacky.

The object of the present invention is thus to overcome the problems described above and to propose a composition that improves the state of the lips during application, but which still remains perceptible even a few days after stopping the application of the composition.

These aims are achieved by the present invention, one subject of which is a cosmetic composition of water-in-oil emulsion type comprising:

from 8% to 70% by weight, relative to the weight of the composition, of an aqueous phase comprising one or more moisturizers or humectants, from 30% to 92% by weight relative to the weight of the composition of a lipophilic phase comprising:
- 1 to 20% by weight relative to the weight of the composition of at least one polar non-volatile hydrocarbon-based first oil,
- at least one volatile or non-volatile, hydrocarbon-based or silicone apolar oil, the composition comprising at least one silicon oil;
- at least one solid compound whose melting point is at least 30° C., chosen from polar or apolar hydrocarbon-based compounds,
- the composition not comprising more than 20% by weight of the lipophilic phase of hydrocarbon-based apolar compound of synthetic origin,
- at least one emulsifying surfactant system for obtaining a water-in-oil emulsion.

A subject of the invention is also a treatment process in which the said composition is applied to the lips.

It has been found, surprisingly, that the effect of improving the suppleness of the lips and the moisturizing sensation remained perceptible several days after stopping the application of the composition.

In addition, the composition according to the invention is easy to apply and leaves a light, non-greasy deposit, which is not tacky.

The terms "between" and "ranging from" should be understood as including the limits.

The composition according to the invention is cosmetic and advantageously comprises a physiologically acceptable medium, i.e. a medium that is particularly suitable for applying a composition of the invention to the lips.

The physiologically acceptable medium is generally adapted to the nature of the support onto which the composition has to be applied, and also to the appearance under which the composition has to be packaged.

Preferably, the composition is in liquid form or in the form of a cream, a butter or a paste.

The viscosity at 20° C. is more particularly greater than 1 Pa·s. Preferably, the composition has a viscosity of between 1 and 25 Pa·s.

The composition according to the invention has, at 20° C., a viscosity of between 1 and 25 Pa·s and preferably between 1.5 and 18 Pa·s.

Preferably, the viscosity at 20° C. of a composition according to the invention is between 2 and 16 Pa·s.

It should be noted that the terms "paste" and "butter" mean a composition that is therefore not solid, and whose viscosity it is possible to measure.

Protocol for Measuring the Viscosity:

The viscosity measurement is performed at 20° C., using a Rheomat RM 180 viscometer equipped with a No. 3 or 4 spindle, the measurement being performed after 10 minutes of rotation of the spindle (after which time stabilization of the viscosity and of the spin speed of the spindle are observed), at a shear rate of 200 $s^{-1}$.

A composition according to the invention is in the form of a water-in-oil emulsion.

Aqueous Phase

The composition according to the invention comprises an aqueous phase whose content is between 15% and 70% by weight relative to the weight of the composition and preferably between 15% and 55% by weight relative to the weight of the composition.

Humectant/Moisturizer

As indicated previously, the composition according to the invention comprises at least one moisturizer (also known as a humectant).

Examples of humectants or moisturizers that may especially be mentioned include:
- polyhydric alcohols, especially of $C_2$-$C_8$ and preferably of $C_3$-$C_6$, comprising from 2 to 6 hydroxyl radicals, such as glycerol, propylene glycol, tripropylene glycol, 1,3-butylene glycol, dipropylene glycol or diglycerol, and a mixture thereof,
- sugars such as sorbitol or xylitol,
- hyaluronic acid and salts thereof, hyaluronic acid spheres such as those sold by the company Engelhard Lyon,
- urea and derivatives thereof, especially Hydrovance (2-hydroxyethylurea) sold by National Starch, AHAs and BHAs, for example lactic acid and salts thereof, especially an alkali metal salt thereof, such as sodium lactate, sodium pidolate, serine, arginine, ectoin and derivatives thereof, chitosan and derivatives thereof, collagen; spheres of collagen and of chondroitin sulfate of marine origin (Atelocollagen) sold by the company Engelhard Lyon under the name marine filling spheres.

plankton, acrylic acid homopolymers such as Lipidure-HM® from NOF Corporation,

β-glucan and in particular sodium carboxymethyl β-glucan from Mibelle-AG-Biochemistry, a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product manufactured by Chimex under the trade name Mexoryl SBB®.

Preferably, the humectant(s)/moisturizer(s) are chosen from polyhydric alcohols, preferably of $C_2$-$C_8$, comprising from 2 to 6 hydroxyl radicals, sugars, urea and derivatives thereof, hyaluronic acid and salts thereof, AHAs, BHAs, in particular lactic acid and the sodium salts thereof, sodium pidolate, serine, arginine, ectoin and derivatives thereof, chitosan and derivatives thereof, collagen, plankton, acrylic acid homopolymers such as Lipidure-HM® from NOF Corporation, and β-glucan.

Even more preferably, the humectant(s)/moisturizer(s) are chosen from polyhydric alcohols, preferably of $C_2$-$C_8$, comprising from 2 to 6 hydroxyl radicals, and most particularly glycerol; hyaluronic acid and salts thereof, and also mixtures thereof.

The composition according to the invention more particularly comprises not more than 10% by weight, relative to the weight of the composition, and preferably from 3% to 10% by weight, relative to the weight of the composition, of moisturizer(s) or humectant(s).

Water-Soluble Solvent

The composition in accordance with the invention may comprise, besides water, at least one water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the compositions according to the invention may also be volatile.

Among the water-soluble solvents that may be used in the compositions in accordance with the invention, mention may be made especially of lower monoalcohols containing from 1 to 5 carbon atoms, such as ethanol and isopropanol, $C_3$ and $C_4$ ketones and $C_2$-$C_4$ aldehydes.

If the composition comprises any, the content of water-soluble solvent(s) represents 0 to 5% by weight relative to the weight of the composition.

Preferably, the aqueous phase of the composition does not comprise any water-soluble solvent.

Lipophilic Phase

The composition thus comprises from 30% to 92% by weight and preferably from 30% to 85% by weight of a lipophilic phase relative to the weight of the composition. In accordance with an even more particular embodiment, the content of lipophilic phase ranges from 40% to 85% by weight and more preferentially from 40% to 75% by weight relative to the weight of the composition.

This lipophilic phase comprises at least one polar non-volatile hydrocarbon-based first oil; at least one volatile or non-volatile, hydrocarbon-based or silicone apolar oil; at least one solid compound whose melting point is at least 30° C., chosen from polar or apolar hydrocarbon-based compounds; at least one emulsifying surfactant system for obtaining a water-in-oil emulsion. Moreover, the composition does not comprise more than 20% by weight of the lipophilic phase of hydrocarbon-based apolar compound of synthetic origin.

The term "hydrocarbon-based apolar compound of synthetic origin" is more particularly intended to denote hydrocarbon-based compounds comprising only hydrogen and carbon atoms, derived from the petrochemical industry, whether these compounds are liquid or solid at room temperature (25° C.).

Polar Hydrocarbon-Based First Oil

The term "oil" means a water-immiscible non-aqueous compound that is liquid at room temperature (25° C.) and at atmospheric pressure ($1.013 \times 10^5$ Pa).

The term "hydrocarbon-based oil" is intended to mean an oil formed essentially from, or even constituted by, carbon and hydrogen atoms, and possibly oxygen and nitrogen atoms, and not containing any silicon or fluorine atoms.

It may contain alcohol, ester, ether, carboxylic acid, amine and/or amide groups.

Preferably, the hydrocarbon-based oil, in addition to being free of silicon and fluorine, is free of heteroatoms such as N, Si and P. The hydrocarbon-based oil is therefore different from a silicone oil and from a fluoro oil.

In the present case, the non-volatile hydrocarbon-based oil comprises at least one oxygen atom.

In particular, this non-volatile hydrocarbon-based oil comprises at least one ester function (it is then called an "ester oil").

The ester oils that may be used in the compositions according to the invention may in particular be hydroxylated.

The composition may comprise one or more non-volatile hydrocarbon-based oils, in particular chosen from:

optionally hydroxylated monoesters, diesters or triesters of a $C_2$-$C_8$ monocarboxylic or polycarboxylic acid and of a $C_2$-$C_8$ alcohol.

In particular:

optionally hydroxylated monoesters of a $C_2$-$C_8$ carboxylic acid and of a $C_2$-$C_8$ alcohol, optionally hydroxylated diesters of a $C_2$-$C_8$ dicarboxylic acid and of a $C_2$-$C_8$ alcohol, such as diisopropyl adipate, 2-diethylhexyl adipate, dibutyl adipate, diisostearyl adipate or 2-diethylhexyl succinate, optionally hydroxylated triesters of a $C_2$-$C_8$ tricarboxylic acid and of a $C_2$-$C_8$ alcohol, such as citric acid esters, such as trioctyl citrate, triethyl citrate, acetyl tributyl citrate, tributyl citrate or acetyl tributyl citrate;

esters of a $C_2$-$C_8$ polyol and of one or more $C_2$-$C_8$ carboxylic acids, such as glycol diesters of monoacids, such as neopentyl glycol diheptanoate, or glycol triesters of monoacids, such as triacetin.

ester oils, in particular containing at least 18 carbon atoms and even more particularly between 18 and 70 carbon atoms.

Examples that may be mentioned include monoesters, diesters or triesters.

The ester oils may be hydroxylated or non-hydroxylated.

The non-volatile ester oil may for example be chosen from:
- monoesters comprising at least 18 carbon atoms and even more particularly containing between 18 and 40 carbon atoms in total, in particular monoesters of formula $R_1COOR_2$ in which $R_1$ represents a linear or branched, saturated or unsaturated or aromatic fatty acid residue comprising from 4 to 40 carbon atoms and $R_2$ represents a hydrocarbon-based chain that is in particular branched, containing from 4 to 40 carbon atoms, on condition that the sum of the carbon atoms of the radicals $R_1$ and $R_2$ is greater than or equal to 18, for instance Purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, isostearyl isostearate, $C_{12}$-$C_{15}$ alkyl benzoates such as 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate or 2-octyldodecyl myristate.

Preferably, they are esters of formula $R_1COOR_2$ in which $R_1$ represents a linear or branched fatty acid residue comprising from 4 to 40 carbon atoms and $R_2$ represents a hydrocarbon-based chain that is in particular branched, containing from 4 to 40 carbon atoms, $R_1$ and $R_2$ being such that the sum of the carbon atoms of the radicals $R_1$ and $R_2$ is greater than or equal to 18.

Even more particularly, the ester comprises between 18 and 40 carbon atoms in total.

Preferred monoesters that may be mentioned include isononyl isononanoate, oleyl erucate and/or 2-octyldodecyl neopentanoate;
- monoesters of a fatty acid, in particular containing at least 18 carbon atoms and even more particularly from 18 to 22 carbon atoms, and especially of lanolic acid, oleic acid, lauric acid or stearic acid, and of diols, for instance propylene glycol monoisostearate.
- diesters especially containing at least 18 carbon atoms and even more particularly comprising between 18 and 60 carbon atoms in total and preferably between 18 and 50 carbon atoms in total. Use may be made especially of diesters of a dicarboxylic acid and of monoalcohols, preferably such as diisostearyl malate, or glycol diesters of monocarboxylic acids, such as neopentyl glycol diheptanoate, propylene glycol dioctanoate, diethylene glycol diisononanoate or polyglyceryl-2 diisostearate (in particular such as the compound sold under the commercial reference Dermol DGDIS by the company Akzo);
- hydroxylated monoesters and diesters, preferably with a total carbon number of at least 18 carbon atoms and even more particularly ranging from 18 to 70, for instance polyglyceryl-3 diisostearate, isostearyl lactate, octyl hydroxystearate, octyldodecyl hydroxystearate, diisostearyl malate or glyceryl stearate;
- triesters especially containing at least 35 carbon atoms and even more particularly comprising between 35 and 70 carbon atoms in total, in particular such as triesters of a tricarboxylic acid, such as triisostearyl citrate, or tridecyl trimellitate, or glycol triesters of monocarboxylic acids such as polyglyceryl-2 triisostearate;
- tetraesters especially containing at least 35 carbon atoms and even more particularly with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityl tetraisononanoate, glyceryl tris(2-decyl)tetradecanoate, polyglyceryl-2 tetraisostearate or pentaerythrityl tetrakis(2-decyl)tetradecanoate;
- polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or else copolymers of polyols and of dimer diacids, and esters thereof, such as Hailucent ISDA;
- esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid especially of $C_8$ to $C_{34}$, especially of $C_{12}$ to $C_{22}$, in particular of $C_{16}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;
- polyesters resulting from the esterification of at least one triglyceride of hydroxylated carboxylic acid(s) with an aliphatic monocarboxylic acid and with an aliphatic dicarboxylic acid, which is optionally unsaturated, for instance the succinic acid and isostearic acid castor oil sold under the reference Zenigloss by Zenitech;
- fatty acid triglycerides, which are in particular saturated, such as heptanoic or octanoic acid triglycerides, caprylic/capric acid triglycerides and mixtures thereof, glyceryl triheptanoate, glyceryl trioctanoate or $C_{18\text{-}36}$ acid triglycerides;
- hydrocarbon-based plant oils such as jojoba oil, unsaturated triglycerides such as castor oil, olive oil, ximenia oil, pracaxi oil, coriander oil, macadamia oil, passionflower oil, argan oil, sesame seed oil, grapeseed oil, avocado oil, apricot kernel oil (*Prunus armeniaca* kernel oil), the liquid fraction of shea butter or the liquid fraction of cocoa butter,
- mixtures thereof.

More particularly, the polar non-volatile first oil included in the composition according to the invention is chosen from monoesters comprising at least 18 carbon atoms, fatty acid triglycerides containing from 7 to 40 carbon atoms, which are liquid at room temperature, and hydrocarbon-based plant oils, and mixtures thereof.

Preferably, the polar non-volatile first oil is chosen from:
- monoesters of formula $R_1COOR_2$ in which $R_1$ represents a linear or branched, saturated or unsaturated, or aromatic fatty acid residue comprising from 4 to 40 carbon atoms and $R_2$ represents a hydrocarbon-based chain that is in particular branched, containing from 4 to 40 carbon atoms, on condition that the sum of the carbon atoms of the radicals $R_1$ and $R_2$ is greater than or equal to 18,
- fatty acid triglycerides, which are in particular saturated, such as heptanoic or octanoic acid triglycerides, caprylic/capric acid triglycerides and mixtures thereof, glyceryl triheptanoate, glyceryl trioctanoate or $C_{18\text{-}36}$ acid triglycerides;
- hydrocarbon-based plant oils such as jojoba oil, unsaturated triglycerides such as castor oil, olive oil, ximenia oil, pracaxi oil, coriander oil, macadamia oil, passionflower oil, argan oil, sesame seed oil, grapeseed oil, avocado oil, apricot kernel oil (*Prunus armeniaca* kernel oil), the liquid fraction of shea butter or the liquid fraction of cocoa butter, mixtures thereof.

According to a particular embodiment of the invention, the content of first oil(s) ranges from 1% to 20% by weight relative to the weight of the composition.

Apolar Oils

The lipophilic phase of the composition according to the invention comprises at least one volatile or non-volatile, hydrocarbon-based or silicone apolar oil.

Non-Volatile Hydrocarbon-Based Apolar Oils

These oils may be of plant, mineral or synthetic origin.

For the purposes of the present invention, the term "apolar oil" more particularly hydrocarbon-based apolar oil, is intended to mean an oil of which the solubility parameter at 25° C., $\delta_a$, is equal to 0 $(J/cm^3)^{1/2}$.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The term "hydrocarbon-based oil" means an oil formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups. The hydrocarbon-based apolar oil is more particularly intended to denote hydrocarbon-based oils comprising only hydrogen and carbon atom.

Preferably, the non-volatile apolar hydrocarbon-based oil may be chosen from linear or branched hydrocarbons of mineral or synthetic origin, such as:

liquid paraffin or derivatives thereof (mineral oil),
squalane,
isoeicosane,
naphthalene oil,
polybutenes such as Indopol H-100 (molar mass or MW=965 g/mol), Indopol H-300 (MW=1340 g/mol) and Indopol H-1500 (MW=2160 g/mol) sold or manufactured by the company Amoco,
polyisobutenes, hydrogenated polyisobutenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), or alternatively Parleam Lite sold by NOF Corporation,
polydecenes and hydrogenated polydecenes such as: Puresyn 10 (MW=723 g/mol) and Puresyn 150 (MW=9200 g/mol) sold or manufactured by the company Mobil Chemicals, or alternatively Puresyn 6 sold by ExxonMobil Chemical),
decene/butene copolymers, polybutene/polyisobutene copolymers, in particular Indopol L-14,
and mixtures thereof.

Preferably, the composition comprises at least one non-volatile apolar hydrocarbon-based oil, more particularly chosen from liquid paraffin or derivatives thereof, and hydrogenated or non-hydrogenated poly(iso)butenes, or mixtures thereof.

Non-phenyl silicone oils

The term "non-phenyl silicone oil" denotes a silicone oil not bearing any phenyl substituents.

Apolar silicon oil is more particularly intended to denote a silicon oil that doesn't comprise any ionic or ionisable group(s), and preferably that doesn't comprise any oxyalkylenated($C_2$-$C_4$) unit(s) (preferably oxyethylene, oxypropylene), or glycerol unit(s).

Representative examples of these non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups.

It should be noted that "dimethicone" (INCI name) corresponds to a poly(dimethylsiloxane) (chemical name).

The non-volatile non-phenyl silicone oil is preferably chosen from non-volatile dimethicone oils.

In particular, these oils can be chosen from the following non-volatile oils:

polydimethylsiloxanes (PDMSs),
PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference Abil Wax 9801 from Evonik Goldschmidt,
PDMSs comprising aliphatic groups, or functional groups such as hydroxyl, thiol and/or amine groups,
polyalkylmethylsiloxanes substituted with functional groups such as hydroxyl, thiol and/or amine groups,
polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular $C_2$-$C_{24}$ alkyl groups, and/or functional groups such as hydroxyl, thiol and/or amine groups.

The non-phenyl silicone oil may be chosen in particular from silicones of formula (I):

$$X-\underset{R_2}{\overset{R_1}{Si}}-O-\left[\underset{R_4}{\overset{R_3}{Si}}-O\right]_n-\left[\underset{R_6}{\overset{R_5}{Si}}-O\right]_p-\underset{R_2}{\overset{R_1}{Si}}-X \quad (I)$$

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular of which the viscosity at 25° C. is between 9 centistokes (cSt) ($9 \times 10^{-6}$ m$^2$/s) and 800 000 cSt.

As non-volatile non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker, the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

Phenyl Silicone Oils Optionally Bearing a Dimethicone Fragment

The term "silicone oil" means an oil containing at least one silicon atom, and in particular containing Si—O groups.

The term "phenyl" specifies that the said oil comprises in its structure a phenyl radical.

The term "dimethicone fragment" denotes a divalent siloxane group in which the silicon atom bears two methyl radicals, this group not being located at the ends of the molecule. It may be represented by the following formula: —(Si(CH$_3$)$_2$—O)—.

The term "non-volatile" is intended to mean an oil of which the vapour pressure at 25° C. and atmospheric pressure is non-zero and is less than 0.02 mmHg (2.66 Pa) and better still less than $10^{-3}$ mmHg (0.13 Pa).

Apolar silicon oil is more particularly intended to denote a silicon oil that doesn't comprise any ionic or ionisable group(s), and preferably that doesn't comprise any oxyalkylenated($C_2$-$C_4$) unit(s) (preferably oxyethylene, oxypropylene), or glycerol unit(s).

The non-volatile phenyl silicone oil may thus be chosen from:

a) phenyl silicone oils optionally bearing a dimethicone fragment corresponding to formula (I) below:

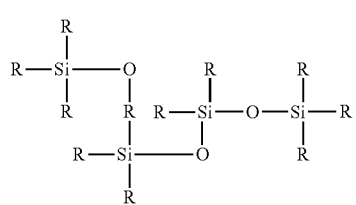

(I)

in which the groups R, which are monovalent or divalent, represent, independently of each other, a methyl or a phenyl, with the proviso that at least one group R represents a phenyl.

Preferably, in this formula, the phenyl silicone oil comprises at least three, for example at least four, at least five or at least six, phenyl groups.

b) phenyl silicone oils optionally bearing a dimethicone fragment corresponding to formula (II) below:

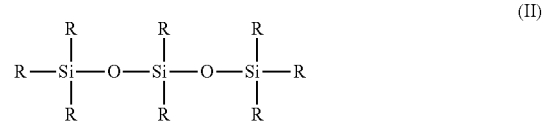

(II)

in which the groups R represent, independently of each other, a methyl or a phenyl, with the proviso that at least one group R represents a phenyl.

Preferably, in this formula, the compound of formula (II) comprises at least three, for example at least four or at least five, phenyl groups.

Mixtures of different phenylorganopolysiloxane compounds described above can be used.

Examples that may be mentioned include mixtures of triphenyl-, tetraphenyl- or pentaphenylorganopolysiloxanes.

Among the compounds of formula (II), mention may more particularly be made of phenyl silicone oils which do not bear a dimethicone fragment, corresponding to formula (II) in which at least 4 or at least 5 radicals R represent a phenyl radical, the remaining radicals representing methyls.

Such non-volatile phenyl silicone oils are preferably trimethylpentaphenyltrisiloxane or tetramethyltetraphenyltrisiloxane. They are in particular sold by Dow Corning under the reference PH-1555 HRI or Dow Corning 555 Cosmetic Fluid (chemical name: 1,3,5-trimethyl-1,1,3,5,5-pentaphenyltrisiloxane; INCI name: trimethylpentaphenyltrisiloxane), or the tetramethyltetraphenyltrisiloxane sold under the reference Dow Corning 554 Cosmetic Fluid by Dow Corning can also be used.

They correspond especially to the following formulae (III), (III'):

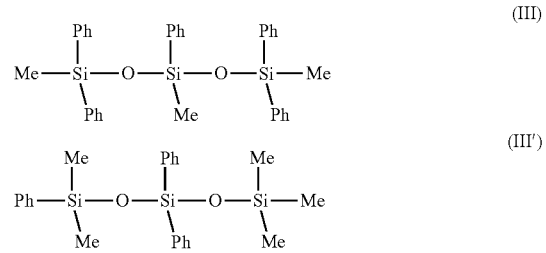

in which Me represents methyl, and Ph represents phenyl.

c) phenyl silicone oils bearing at least one dimethicone fragment corresponding to formula (IV) below:

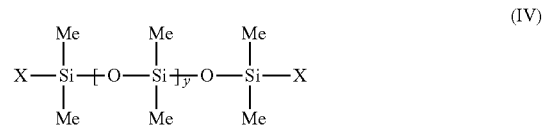

(IV)

in which Me represents methyl, y is between 1 and 1000 and X represents —CH$_2$—CH(CH$_3$)(Ph).

d) phenyl silicone oils corresponding to formula (V) below, and mixtures thereof:

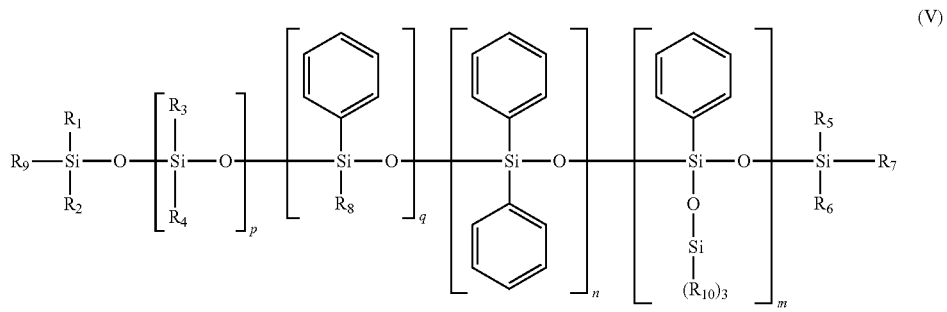

in which:
- $R_1$ to $R_{10}$, independently of each other, are saturated or unsaturated, linear, cyclic or branched $C_1$-$C_{30}$ hydrocarbon-based radicals,
- m, n, p and q are, independently of each other, integers between 0 and 900, with the proviso that the sum m+n+q is other than 0.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$, independently of each other, represent a saturated or unsaturated, preferably saturated, linear or branched $C_1$-$C_{30}$ hydrocarbon-based radical, and in particular a preferably saturated, $C_1$-$C_{20}$, in particular $C_1$-$C_{18}$, hydrocarbon-based radical, or a monocyclic or polycyclic $C_6$-$C_{14}$, and in particular $C_{10}$-$C_{13}$, aryl radical, or an aralkyl radical, the alkyl part of which is preferably $C_1$-$C_3$ alkyl.

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may in particular be identical, and in addition may be a methyl radical.

According to a first more particular embodiment of formula (V), mention may be made of:
i) phenyl silicone oils optionally bearing at least one dimethicone fragment corresponding to formula (VI) below, and mixtures thereof:

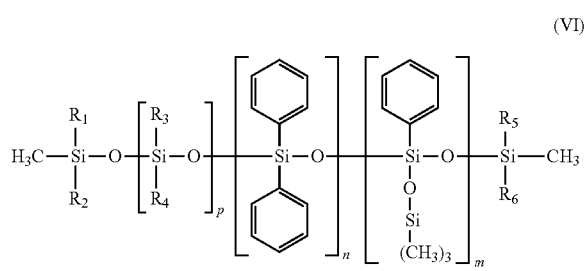

in which:
- $R_1$ to $R_6$, independently of each other, are saturated or unsaturated, linear, cyclic or branched $C_1$-$C_{30}$ hydrocarbon-based radicals, a preferably $C_6$-$C_{14}$ aryl radical or an aralkyl radical, the alkyl part of which is $C_1$-$C_3$ alkyl,
- m, n and p are, independently of each other, integers between 0 and 100, with the proviso that the sum n+m is between 1 and 100.

Preferably, $R_1$ to $R_6$, independently of each other, represent a $C_1$-$C_{20}$, in particular $C_1$-$C_{18}$, hydrocarbon-based, preferably alkyl, radical, or a $C_6$-$C_{14}$ aryl radical which is monocyclic (preferably $C_6$) or polycyclic and in particular $C_{10}$-$C_{13}$, or an aralkyl radical (preferably the aryl part is $C_6$ aryl; the alkyl part is $C_1$-$C_3$ alkyl).

Preferably, $R_1$ to $R_6$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may in particular be identical, and in addition may be a methyl radical. Preferably, m=1 or 2 or 3, and/or n=0 and/or p=0 or 1 can be applied, in formula (VI).

According to one particular embodiment, the non-volatile phenyl silicone oil is chosen from phenyl silicone oils bearing at least one dimethicone fragment.

Preferably, such oils correspond to compounds of formula (VI) in which:
A) m=0 and n and p are, independently of each other, integers between 1 and 100.

Preferably, $R_1$ to $R_6$ are methyl radicals.

According to this embodiment, the silicone oil is preferably chosen from a diphenyl dimethicone such as KF-54 from Shin Etsu (400 cSt), KF54HV from Shin Etsu (5000 cSt), KF-50-300CS from Shin Etsu (300 cSt), KF-53 from Shin Etsu (175 cSt) or KF-50-100CS from Shin Etsu (100 cSt).

B) p is between 1 and 100, the sum n+m is between 1 and 100, and n=0.

These phenyl silicone oils optionally bearing at least one dimethicone fragment correspond more particularly to formula (VII) below:

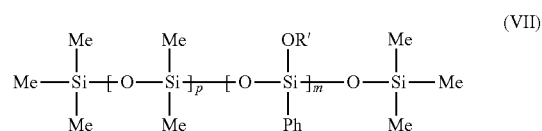

in which Me is methyl and Ph is phenyl, OR' represents a group —$OSiMe_3$ and p is 0 or is between 1 and 1000, and m is between 1 and 1000. In particular, m and p are such that the compound (VII) is a non-volatile oil.

According to a first embodiment of non-volatile phenyl silicone bearing at least one dimethicone fragment, p is between 1 and 1000 and m is more particularly such that the compound (VII) is a non-volatile oil. Trimethylsiloxyphenyldimethicone, sold in particular under the reference Belsil PDM 1000 by the company Wacker, may, for example, be used.

According to a second embodiment of non-volatile phenyl silicone not bearing a dimethicone fragment, p is equal to 0 and m is between 1 and 1000, and in particular is such that the compound (VII) is a non-volatile oil.

Phenyltrimethylsiloxytrisiloxane, sold in particular under the reference Dow Corning 556 Cosmetic Grade Fluid (DC556), may, for example, be used.

ii) non-volatile phenyl silicone oils not bearing a dimethicone fragment corresponding to formula (VIII) below, and mixtures thereof:

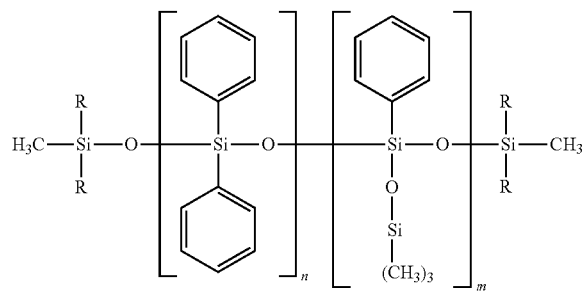

(VIII)

in which:
R, independently of each other, are saturated or unsaturated, linear, cyclic or branched $C_1$-$C_{30}$ hydrocarbon-based radicals, preferably R is a $C_1$-$C_{30}$ alkyl radical, a preferably $C_6$-$C_{14}$ aryl radical, or an aralkyl radical, the alkyl part of which is $C_1$-$C_3$ alkyl,
m and n are, independently of each other, integers between 0 and 100, with the proviso that the sum n+m is between 1 and 100.

Preferably, R, independently of each other, represent a saturated or unsaturated, preferably saturated, linear or branched $C_1$-$C_{30}$ hydrocarbon-based radical, and in particular a preferably saturated, $C_1$-$C_{20}$, in particular $C_1$-$C_{18}$ and more particularly $C_4$-$C_{10}$, hydrocarbon-based radical, a monocyclic or polycyclic $C_6$-$C_{14}$, and in particular $C_{10}$-$C_{13}$, aryl radical, or an aralkyl radical of which preferably the aryl part is $C_6$ aryl and the alkyl part is $C_1$-$C_3$ alkyl.

Preferably, the Rs may each represent a methyl, ethyl, propyl, butyl, isopropyl, decyl, dodecyl or octadecyl radical, or alternatively a phenyl, tolyl, benzyl or phenethyl radical.

The Rs may in particular be identical, and in addition may be a methyl radical.

Preferably, m=1 or 2 or 3, and/or n=0 and/or p=0 or 1 can be applied, in formula (VIII).

According to one preferred embodiment, n is an integer between 0 and 100 and m is an integer between 1 and 100, with the proviso that the sum n+m is between 1 and 100, in formula (VIII). Preferably, R is a methyl radical.

According to one embodiment, a phenyl silicone oil of formula (VIII) with a viscosity at 25° C. of between 5 and 1500 mm²/s (i.e. 5 to 1500 cSt), and preferably with a viscosity of between 5 and 1000 mm²/s (i.e. 5 to 1000 cSt), may be used.

According to this embodiment, the non-volatile phenyl silicone oil is preferably chosen from phenyl trimethicones (when n=0) such as DC556 from Dow Corning (22.5 cSt), or else from diphenylsiloxyphenyl trimethicone oil (when m and n are between 1 and 100) such as KF56 A from Shin Etsu, or the Silbione 70663V30 oil from Rhone-Poulenc (28 cSt). The values in parentheses represent the viscosities at 25° C.

e) phenyl silicone oils optionally bearing at least one dimethicone fragment corresponding to the following formula, and mixtures thereof:

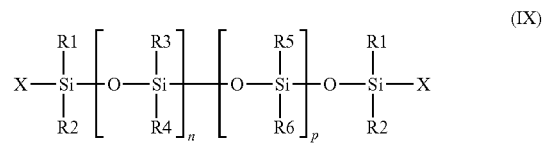

(IX)

in which:
$R_1$, $R_2$, $R_5$ and $R_6$, which may be identical or different, are an alkyl radical containing 1 to 6 carbon atoms,
$R_3$ and $R_4$, which may be identical or different, are an alkyl radical containing from 1 to 6 carbon atoms or an aryl radical (preferably $C_6$-$C_{14}$), with the proviso that at least one of $R_3$ and $R_4$ is a phenyl radical,
X is an alkyl radical containing from 1 to 6 carbon atoms, a hydroxyl radical or a vinyl radical,
n and p being an integer greater than or equal to 1, chosen so as to give the oil a weight-average molecular weight of less than 200 000 g/mol, preferably less than 150 000 g/mol and more preferably less than 100 000 g/mol.

f) and a mixture thereof.

Preferably, the composition according to the invention comprises at least one non-volatile phenyl silicone oil, more particularly not containing any dimethicone fragments.

Volatile Oils

According to a particular embodiment of the invention, the composition may also comprise at least one volatile oil.

The volatile oil may in particular be a silicone oil, a hydrocarbon-based oil, which is preferably apolar, or a fluoro oil.

According to one embodiment, the volatile oil is a silicone oil and may be chosen in particular from silicone oils with a flash point ranging from 40° C. to 102° C., preferably with a flash point of greater than 55° C. and less than or equal to 95° C., and preferentially ranging from 65° C. to 95° C.

As volatile silicone oils that may be used in the invention, mention may be made of linear or cyclic silicones with a viscosity at room temperature of less than 8 centistokes (cSt) ($8 \times 10^{-6}$ m²/s), and in particular containing from 2 to 10 silicon atoms and in particular from 2 to 7 silicon atoms, these silicones optionally comprising alkyl or alkoxy groups containing from 1 to 10 carbon atoms.

As volatile silicone oils that may be used in the invention, mention may be made in particular of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to a second embodiment, the volatile oil is a fluoro oil, such as nonafluoromethoxybutane or perfluoromethylcyclopentane, and mixtures thereof.

According to a third embodiment, the volatile oil is a hydrocarbon-based oil, which is preferably apolar.

The apolar volatile hydrocarbon-based oil may have a flash point ranging from 40° C. to 102° C., preferably ranging from 40° C. to 55° C. and preferentially ranging from 40° C. to 50° C.

The hydrocarbon-based volatile oil may in particular be chosen from hydrocarbon-based volatile oils containing from 8 to 16 carbon atoms, and mixtures thereof, and in particular:

branched $C_8$-$C_{16}$ alkanes such as $C_8$-$C_{16}$ isoalkanes (also known as isoparaffins), isododecane, isodecane and isohexadecane, and, for example, the oils sold under the trade name Isopar or Permethyl, linear alkanes, for instance n-dodecane and n-tetradecane sold by Sasol under the respective references Parafol 12-97 and Parafol 14-97, and also mixtures thereof, the undecane-tridecane mixture (Cetiol UT), the mixtures of n-undecane and of n-tridecane obtained in Examples 1 and 2 of patent application WO 2008/155 059 from the company Cognis, and mixtures thereof Preferably, the composition according to the invention comprises at least one phenyl silicone oil, optionally bearing dimethicone fragment(s), and preferably not comprising any.

According to this preferred embodiment, the composition also comprises one or more volatile silicone oils.

Moreover, the composition may also preferably comprise at least one apolar hydrocarbon-based oil, more particularly chosen from hydrogenated or non-hydrogenated poly(iso) butenes.

In accordance with a particular embodiment of the invention, the content of volatile or non-volatile, hydrocarbon-based or silicone apolar oil more particularly ranges from 5% to 40% by weight and preferably from 8% to 30% by weight relative to the weight of the composition; the composition comprising not more than 20% by weight of the lipophilic phase of hydrocarbon-based apolar compound of synthetic origin.

More particularly, the non-volatile silicone oil/volatile silicone oil weight ratio, when these oils are present in the composition, ranges from 0.1 to 2.

Solid Compounds

As has been mentioned previously, the lipophilic phase of the composition comprises at least one solid compound whose melting point is at least 30° C., preferably between 30° C. and 100° C., chosen from polar or apolar hydrocarbon-based compounds.

These solid compounds may be chosen from waxes and pasty compounds.

Waxes

The composition according to the invention may comprise at least one wax.

The waxes that may be used in a composition according to the invention are chosen from solid waxes that may or may not be deformable at room temperature of animal, plant, mineral or synthetic origin, and mixtures thereof For the purposes of the invention, the term "wax" means a lipophilic compound, which is solid at room temperature (25° C.), with a reversible solid/liquid change of state, which has a melting point of greater than or equal to 30° C., which may be up to 100° C.

For the purposes of the invention, the melting point corresponds to the temperature of the most endothermic peak observed in thermal analysis (DSC) as described in the standard ISO 11357-3; 1999. The melting point of the wax may be measured using a differential scanning calorimeter (DSC), for example the calorimeter sold under the name DSC Q2000 by the company TA Instruments.

Preferably, the waxes have a heat of fusion ΔHf of greater than or equal to 70 J/g.

Preferably, the waxes comprise at least one crystallizable part, which is visible by X-ray observations.

The measurement protocol is as follows:

A sample of 5 mg of wax placed in a crucible is subjected to a first temperature rise passing from −20° C. to 120° C., at a heating rate of 10° C./minute, it is then cooled from 120° C. to −20° C. at a cooling rate of 10° C./minute and is finally subjected to a second temperature increase passing from −20° C. to 120° C. at a heating rate of 5° C./minute. During the second temperature increase, the following parameters are measured:

the melting point (Mp) of the wax, as mentioned previously corresponding to the temperature of the most endothermic peak of the melting curve observed, representing the variation in the difference in power absorbed as a function of the temperature, ΔHf: the heat of fusion of the wax, corresponding to the integral entire melting curve obtained. This heat of fusion of the wax is the amount of energy required to make the compound change from the solid state to the liquid state. It is expressed in J/g.

The wax may especially have a hardness ranging from 0.05 MPa to 15 MPa and preferably ranging from 6 MPa to 15 MPa. The hardness is determined by measuring the compression force, measured at 20° C. using the texturometer sold under the name TA-TX2i by the company Rheo, equipped with a stainless-steel cylinder 2 mm in diameter travelling at a measuring speed of 0.1 mm/s, and penetrating the wax to a penetration depth of 0.3 mm.

Apolar Waxes:

The term "apolar wax" means a wax whose solubility parameter at 25° C. as defined below, $\delta_a$, is equal to 0 $(J/cm^3)^{1/2}$.

Apolar waxes are in particular hydrocarbon-based waxes constituted solely of carbon and hydrogen atoms, and free of heteroatoms such as N, O, Si and P.

The term "hydrocarbon-based wax" means a wax formed essentially from, or even constituted of, carbon and hydrogen atoms, and optionally oxygen and nitrogen atoms, and that does not contain any silicon or fluorine atoms. It may contain alcohol, ester, ether, carboxylic acid, amine and/or amide groups.

More particularly, the apolar wax may be chosen from microcrystalline waxes, paraffin waxes, ozokerite, polyethylene waxes, polymethylene waxes and microwaxes, and mixtures thereof.

As microcrystalline waxes that may be used, mention may be made of Multiwax W 445® sold by the company Sonneborn, and Microwax HW® and Base Wax 30540® sold by the company Paramelt.

An ozokerite that may be mentioned is Ozokerite Wax SP 1020 P.

Polyethylene waxes that may be mentioned include Performalene 500-L Polyethylene and Performalene 400 Polyethylene sold by New Phase Technologies.

Polymethylene waxes that may be mentioned include the Polymethylene Wax (54° C.) sold under the reference Cirebelle 303; the Polymethylene Wax (80° C.) sold under the reference Cirebelle 108, sold by Cirebelle.

As microwaxes that may be used in the compositions according to the invention as apolar wax, mention may be made especially of polyethylene microwaxes such as those sold under the names Micropoly 200®, 220®, 220L® and 250S® by the company Micro Powders.

Polar Waxes

For the purposes of the present invention, the term "polar wax" means a wax whose solubility parameter at 25° C., $\delta_a$, is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: *The three -dimensional solubility parameters* , J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

The polar waxes may especially be hydrocarbon-based, fluoro or silicone waxes.

The term "silicone wax" means an oil comprising at least one silicon atom, and especially comprising Si—O groups.

According to a first embodiment, the polar wax is a hydrocarbon-based wax. As a hydrocarbon-based polar wax, a wax chosen from ester waxes and alcohol waxes is in particular preferred.

According to the invention, the term "ester wax" means a wax comprising at least one ester function.

The expression "alcohol wax" is understood according to the invention to mean a wax comprising at least one alcohol function, i.e. comprising at least one free hydroxyl (OH) group.

The following may especially be used as ester wax:

ester waxes such as those chosen from:

i) waxes of formula $R_1COOR_2$ in which $R_1$ and $R_2$ represent linear, branched or cyclic aliphatic chains in which the number of atoms ranges from 10 to 50, which may contain a heteroatom such as O , N or P and whose melting point ranges from 25 to 120° C.

In particular, use may be made, as ester wax, of a $C_{20}$-$C_{40}$ alkyl (hydroxystearyloxy)stearate (the alkyl group comprising from 20 to 40 carbon atoms), alone or as a mixture, or a $C_{20}$-$C_{40}$ alkyl stearate. Such waxes are especially sold under the names Kester Wax K 82 P®, Hydroxypolyester K 82 P®, Kester Wax K 80 P® and Kester Wax K82H by the company Koster Keunen.

ii) glycol and butylene glycol montanate (octacosanoate) waxes such as the wax Licowax KPS Flakes (ICI name: glycol montanate) sold by the company Clariant.

iii) bis(1,1,1-trimethylolpropane) tetrastearate, sold under the name Hest 2T-4S® by the company Heterene.

iv) diester waxes of a dicarboxylic acid of general formula $R^3$—(—OCO—$R^4$—COO—$R^5$), in which $R^3$ and $R^5$ are identical or different, preferably identical and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturated groups, and preferably that is linear and unsaturated.

v) Mention may also be made of the waxes obtained by catalytic hydrogenation of animal or vegetable oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax Ricin 16L64® and 22L73® by the company Sophim. Such waxes are described in patent application FR-A-2792190 and the waxes obtained by hydrogenation of olive oil esterified with stearyl alcohol such as that sold under the name Phytowax Olive 18 L 57, or else;

vi) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax; montan wax, orange wax, laurel wax and hydrogenated jojoba wax, silicone waxes obtained by esterification with a (poly) alkoxylated silicone, such as silicone beeswax, silicone candelilla wax or silicone carnauba wax, and mixtures thereof.

Alcohol waxes that may be mentioned include alcohols, which are preferably linear and preferably saturated, comprising from 16 to 60 carbon atoms, with a melting point of between 25 and 120° C. Examples that may be mentioned include the wax Performacol 550-L Alcohol from New Phase Technologies, stearyl alcohol, cetyl alcohol, myristyl alcohol, palmityl alcohol, behenyl alcohol, erucyl alcohol or arachidyl alcohol, or mixtures thereof.

Pasty Compounds

The composition under consideration according to the invention may also comprise at least one pasty fatty substance.

For the purposes of the present invention, the term "pasty fatty substance" means a lipophilic fatty compound with a reversible solid/liquid change of state, exhibiting an anisotropic crystalline organization in the solid state, and comprising, at a temperature of 23° C., a liquid fraction and a solid fraction.

In other words, the starting melting point of the pasty compound can be less than 23° C. The liquid fraction of the pasty compound measured at 23° C. can represent 9% to 97% by weight of the compound. This liquid fraction at 23° C. preferably represents between 15% and 85% and more preferably between 40% and 85% by weight.

For the purposes of the invention, the melting point corresponds to the temperature of the most endothermic peak observed in thermal analysis (DSC) as described in the standard ISO 11357-3; 1999. The melting point of a paste or of a wax may be measured using a differential scanning calorimeter (DSC), for example the calorimeter sold under the name MDSC 2920 by the company TA Instruments.

The measurement protocol is as follows:

A sample of 5 mg of paste or wax (depending on the case) placed in a crucible is subjected to a first temperature rise passing from −20° C. to 100° C., at the heating rate of 10° C./minute, then is cooled from 100° C. to −20° C. at a cooling rate of 10° C./minute and finally subjected to a second temperature rise passing from −20° C. to 100° C. at a heating rate of 5° C./minute. During the second temperature rise, the variation in the difference between the power absorbed by the empty crucible and the crucible containing the sample of paste or wax as a function of the temperature is measured. The melting point of the compound is the value of the temperature corresponding to the top of the peak of the curve representing the variation in the difference in power absorbed as a function of the temperature.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to change from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., composed of a liquid fraction and a solid fraction.

The liquid fraction of the pasty compound measured at 32° C. preferably represents from 30% to 100% by weight of the compound, preferably from 50% to 100% and more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

The pasty fatty substance may be chosen from synthetic compounds and compounds of plant origin. A pasty fatty substance may be obtained by synthesis from starting materials of plant origin.

The pasty compound is advantageously chosen from:
lanolin and derivatives thereof, such as lanolin alcohol, oxyethylenated lanolins, acetylated lanolin, lanolin esters such as isopropyl lanolate, and oxypropylenated lanolins,
petroleum jelly, in particular the product whose INCI name is petrolatum and which is sold under the name Ultima White PET USP by the company Penreco,
polyol ethers chosen from polyalkylene glycol pentaerythrityl ether, fatty alcohol ethers of sugar, and mixtures thereof, the polyethylene glycol pentaerythrityl ether comprising 5 oxyethylene units (5 OE) (CTFA name: PPG-5 Pentaerythrityl Ether), polypropylene glycol pentaerythrityl ether comprising five oxypropylene (5 OP) units (CTFA name: PEG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil;
liposoluble polyethers resulting from polyetherification between one or more $C_2$-$C_{100}$ and preferably $C_2$-$C_{50}$ diols.
Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.
esters and polyesters,
and/or mixtures thereof.
Among the esters, the following are especially preferred:
esters of glycerol oligomers, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, preferably such as bisdiglyceryl polyacyladipate-2 sold under the brand name Softisan 649 by the company Sasol,
vinyl ester homopolymers bearing $C_8$-$C_{30}$ alkyl groups, such as polyvinyl laurate (sold especially under the reference Mexomer PP by the company Chimex) and arachidyl propionate sold under the brand name Waxeno1801 by Alzo,
phytosterol esters,
fatty acid triglycerides and derivatives thereof, for instance triglycerides of fatty acid, which are especially $C_{10}$-$C_{18}$, and partially or totally hydrogenated such as those sold under the reference Softisan 100 by the company Sasol,
pentaerythritol esters,
non-crosslinked polyesters resulting from polycondensation between a linear or branched $C_4$-$C_{50}$ dicarboxylic acid or polycarboxylic acid and a $C_2$-$C_{50}$ diol or polyol,
aliphatic esters of an ester resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid comprising from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:
a) partial or total esters of saturated linear monohydroxylated aliphatic monocarboxylic acids;
b) partial or total esters of unsaturated monohydroxylated aliphatic monocarboxylic acids;
c) partial or total esters of saturated monohydroxylated aliphatic polycarboxylic acids;
d) partial or total esters of saturated polyhydroxylated aliphatic polycarboxylic acids;
e) partial or total esters of $C_2$ to $C_{16}$ aliphatic polyols that have reacted with a monohydroxylated or polyhydroxylated aliphatic monocarboxylic or poly-carboxylic acid, and mixtures thereof

- esters of diol dimer and of diacid dimer, where appropriate esterified on the free alcohol or acid function(s) thereof with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool S), and mixtures thereof,
- butters of plant origin, such as mango butter, such as the product sold under the reference Lipex 203 by the company Aarhuskarlshamn, shea butter, in particular the product whose INCI name is Butyrospermum Parkii Butter, such as the product sold under the reference Sheasoft® by the company Aarhuskarlshamn, cupuacu butter (Rain Forest RF3410 from the company Beraca Sabara), murumuru butter (Rain Forest RF3710 from the company Beraca Sabara), cocoa butter; and also orange wax, for instance the product sold under the reference Orange Peel Wax by the company Koster Keunen,
- totally or partially hydrogenated plant oils, for instance hydrogenated soybean oil, hydrogenated coconut oil, hydrogenated rapeseed oil, mixtures of hydrogenated plant oils such as the mixture of hydrogenated soybean, coconut, palm and rapeseed plant oil, for example the mixture sold under the reference Akogel® by the company Aarhuskarlshamn (INCI name Hydrogenated Vegetable Oil), the trans-isomerized partially hydrogenated jojoba oil manufactured or sold by the company Desert Whale under the commercial reference Iso-Jojoba-50®, partially hydrogenated olive oil, for instance the compound sold under the reference Beurrolive by the company Soliance,
- hydrogenated castor oil esters, such as hydrogenated castor oil dimer dilinoleate, for example Risocast-DA-L sold by Kokyu Alcohol Kogyo, and hydrogenated castor oil isostearate, for example Salacos HCIS (V-L) sold by Nisshin Oil, and mixtures thereof.

Among the pasty compounds, liposoluble polyethers, esters and polyesters more particularly with esters of glycerol oligomers, butters of plant origin and totally or partially hydrogenated plant oils will preferably be chosen.

In accordance with a particularly preferred embodiment of the invention, the composition comprises at least one wax.

Preferably, the content of solid compound(s) ranges from 0.15% to 20% by weight relative to the weight of the composition.

Surfactant System

The composition according to the invention comprises at least one emulsifying surfactant system, more particularly chosen from fatty acid esters of polyols such as sorbitol or glyceryl mono-, di-, tri- or sesqui-oleates or -stearates, glyceryl or polyethylene glycol laurates; silicone surfactants such as alkyl or alkoxy dimethicone copolyols with an alkyl or alkoxy chain that is pendent or at the end of the silicone backbone, for example containing from 6 to 22 carbon atoms; polymers of the polyoxyalkylenated glycol fatty acid ester type.

The composition according to the invention comprises an emulsifying surfactant that makes it possible to obtain a water-in-oil emulsion, especially a surfactant with an HLB (hydrophilic/lipophilic balance) of less than 7.

Preferably, the emulsifying surfactant is chosen from fatty acid esters of polyols such as sorbitol or glyceryl mono-, di-, tri- or sesqui-oleates or -stearates, glyceryl or polyethylene glycol laurates; alkyl or alkoxy dimethicone copolyols with an alkyl or alkoxy chain that is pendent or at the end of the silicone backbone, for example containing from 6 to 22 carbon atoms; polymers of the polyoxyalkylenated glycol fatty acid ester type, and mixtures thereof.

Preferably, the composition comprises at least one silicone surfactant.

Preferably, the composition comprises at least one surfactant chosen from alkyl or alkoxy dimethicone copolyols with an alkyl or alkoxy chain that is pendent or at the end of the silicone backbone, for example containing from 6 to 22 carbon atoms.

In particular, the emulsifying surfactant may be a $C_8$-$C_{22}$ alkyl dimethicone copolyol, i.e. an oxypropylenated and/or oxyethylenated polymethyl($C_8$-$C_{22}$)alkyldimethylmethylsiloxane.

The $C_8$-$C_{22}$ alkyl dimethicone copolyol is advantageously a compound of formula (I) below:

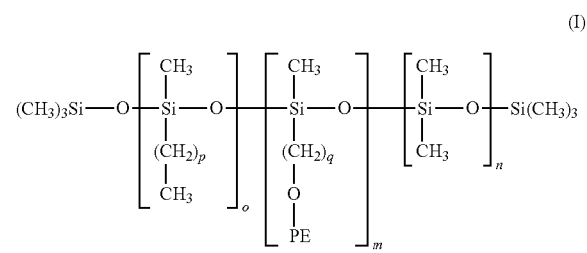

in which:
PE represents $(-C_2H_4O)_x-(C_3H_6O)_y-R$, R being chosen from a hydrogen atom and an alkyl radical of 1 to 4 carbon atoms, x ranging from 0 to 100 and y ranging from 0 to 80, x and y not simultaneously being 0
m ranging from 1 to 40
n ranging from 10 to 200
o ranging from 1 to 100
p ranging from 7 to 21
q ranging from 0 to 4
and preferably:
R=H
m=1 to 10
n=10 to 100
o=1 to 30
p=15
q=3.

Preferably, as $C_8$-$C_{22}$ alkyl dimethicone copolyol, use is made of cetyl dimethicone copolyol, especially the product whose INCI name is Cetyl PEG/PPG-10/1 Dimethicone, for instance the product sold under the name Abil EM-90 by the company Evonik Goldschmidt.

As another surfactant that may be used in the invention to obtain a W/O emulsion, mention may be made of polymers of the polyoxyalkylenated glycol fatty acid ester type with water-in-oil emulsifying properties.

The fatty acid ester of the said polymer is preferably polyhydroxylated. In particular, this polymer is a block polymer, preferably of ABA structure, comprising poly (hydroxylated ester) blocks and polyethylene glycol blocks.

The fatty acid ester of the said emulsifying polymer as defined above generally bears a chain comprising from 12 to 20 carbon atoms and preferably from 14 to 18 carbon atoms. The esters may be chosen especially from oleates, palmitates and stearates.

The polyethylene glycol blocks of the said emulsifying polymer as defined above preferably comprise from 4 to 50 mol of ethylene oxide and more preferably from 20 to 40 mol of ethylene oxide.

A polymeric surfactant that is particularly suitable for preparing the compositions of the invention is polyethylene glycol dipolyhydroxystearate with 30 OE, sold under the trade name Arlacel P 135 by the company ICI.

Advantageously, the surfactant may be chosen from the group comprising polyol alkyl esters. Polyol alkyl esters that may especially be mentioned include glycerol and/or sorbitan esters, for example the polyglyceryl-3 diisostearate sold under the name Lameform TGI by the company Cognis, polyglyceryl-4 isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

Needless to say, the composition according to the invention may comprise several surfactants. In particular, the composition according to the invention may comprise a mixture of at least two surfactants chosen from fatty acid esters of polyols such as sorbitol or glyceryl mono-, di-, tri- or sesqui-oleates or -stearates, glyceryl or polyethylene glycol laurates; alkyl or alkoxy dimethicone copolyols with an alkyl or alkoxy chain that is pendent or at the end of the silicone backbone, for example containing from 6 to 22 carbon atoms; polymers of the polyoxyalkylenated glycol fatty acid ester type, and mixtures thereof.

According to a particularly preferred embodiment, the composition according to the invention comprises a silicone surfactant, preferably chosen from the $C_8$-$C_{22}$ alkyl dimethicone copolyols of formula (I), preferably cetyl dimethicone copolyol, especially the product whose INCI name is Cetyl PEG/PPG-10/1 Dimethicone, for instance the product sold under the name Abil EM-90 by the company Evonik Goldschmidt.

Preferably, according to this embodiment, the composition according to the invention comprises at least one cosurfactant chosen from polyol alkyl esters, preferably from glycerol and/or sorbitan esters. Preferably, the cosurfactant is chosen from polyglyceryl-3 diisostearate, polyglyceryl-4 isostearate, sorbitan isostearate and sorbitan glyceryl isostearate, and mixtures thereof.

Preferably, the cosurfactant is polyglyceryl-4 isostearate, such as the product sold under the name Isolan GI 34 by the company Goldschmidt.

The emulsifying surfactant system may be present in the composition in a content ranging from 1% to 6% by weight and preferably ranging from 2% to 6% by weight relative to the total weight of the composition.

A composition according to the invention may also comprise any additional component usually used in cosmetics, such as dyestuffs, fillers or cosmetic active agents.

Needless to say, a person skilled in the art will take care to select the optional additional compounds and/or the amount thereof such that the advantageous properties of the composition used according to the invention are not, or are not substantially, adversely affected by the envisaged addition.

Dyestuffs

A composition in accordance with the present invention may comprise at least one dyestuff, which may be chosen from water-soluble or water-insoluble, liposoluble or non-liposoluble, organic or mineral dyestuffs, and materials with an optical effect, and mixtures thereof. Preferably, the amount of dyestuff is below 10% by weight relative to the total weight of the said composition.

For the purposes of the present invention, the term "dyestuff" means a compound that is capable of producing a coloured optical effect when it is formulated in sufficient amount in a suitable cosmetic medium.

Preferably, the composition according to the invention comprises at least one dyestuff, chosen from pigments and/or nacres and/or water-soluble dyes, and mixtures thereof.

According to one preferred embodiment, a composition according to the invention comprises at least one water-soluble dyestuff.

The water-soluble dyestuffs used according to the invention are more particularly water-soluble dyes.

For the purposes of the invention, the term "water-soluble dye" is intended to mean any natural or synthetic, generally organic compound, which is soluble in an aqueous phase or water-miscible solvents and which is capable of colouring. In particular, the term "water-soluble" is intended to mean the capacity of a compound to be dissolved in water, measured at 25° C., to a concentration at least equal to 0.1 g/l (production of a macroscopically isotropic, transparent, coloured or colourless solution). This solubility is in particular greater than or equal to 1 g/l.

As water-soluble dyes that are suitable for use in the invention, mention may be made in particular of synthetic or natural water-soluble dyes, for instance FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570), FDC Blue 1 (CI: 42090).

As non-limiting illustrations of sources of water-soluble dyestuff(s) that may be used in the context of the present invention, mention may be made especially of those of natural origin, such as extracts of cochineal carmine, of beetroot, of grape, of carrot, of tomato, of annatto, of paprika, of henna, of caramel and of curcumin.

Thus, the water-soluble dyestuffs that are suitable for use in the invention are especially carminic acid, betanin, anthocyans, enocyanins, lycopene, β-carotene, bixin, norbixin, capsanthin, capsorubin, flavoxanthin, lutein, cryptoxanthin, rubixanthin, violaxanthin, riboflavin, rhodoxanthin, cantaxanthin and chlorophyll, and mixtures thereof.

They may also be copper sulfate, iron sulfate, water-soluble sulfopolyesters, rhodamine, betaine, methylene blue, the disodium salt of tartrazine and the disodium salt of fuchsin.

Some of these water-soluble dyestuffs are in particular permitted for food use. Representatives of these dyes that may be mentioned more particularly include dyes of the carotenoid family, referenced under the food codes E120, E162, E163, E160a-g, E150a, E101, E100, E140 and E141.

According to one preferred variant, the water-soluble dyestuff(s) that are to be transferred onto the skin and/or the lips intended to be made up are formulated in a physiologically acceptable medium so as to be compatible with impregnation into the substrate.

The water-soluble dyestuff(s) may be present in a composition according to the invention in a content ranging from 0.001% to 5% by weight and preferably from 0.002% to 3% by weight relative to the total weight of the said composition.

According to another embodiment, the composition according to the invention may comprise at least one pigment and/or nacre as dyestuff.

The term "pigments" should be understood as meaning white or coloured, inorganic (mineral) or organic particles, which are insoluble in the liquid organic phase, and which are intended to colour and/or opacify the composition and/or the deposit produced with the composition.

The pigments may be chosen from mineral pigments, organic pigments and composite pigments (i.e. pigments based on mineral and/or organic materials).

The pigments may be chosen from monochromatic pigments, lakes, nacres, and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue and ferric blue, and mixtures thereof The organic pigments may be, for example:
cochineal carmine,
organic pigments of azo dyes, anthraquinone dyes, indigoid dyes, xanthene dyes, pyrene dyes, quinoline dyes, triphenylmethane dyes or fluoran dyes,
organic lakes or insoluble sodium, potassium, calcium, barium, aluminum, zirconium, strontium or titanium salts of acidic dyes such as azo, anthraquinone, indigoid, xanthene, pyrene, quinoline, triphenylmethane or fluoran dyes. These dyes generally comprise at least one carboxylic or sulfonic acid group;
melanin-based pigments.

Among the organic pigments, mention may be made of D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 and FD&C Yellow No. 6.

The hydrophobic treatment agent may be chosen from silicones such as methicones, dimethicones and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxane s comprising perfluoroalkyl perfluoropolyether groups, amino acids, N-acylamino acids or salts thereof; lecithin, isopropyl triisostearyl titanate, and mixtures thereof.

The N-acylamino acids can comprise an acyl group containing from 8 to 22 carbon atoms, such as, for example, a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine The term "alkyl" mentioned in the compounds cited above especially denotes an alkyl group containing from 1 to 30 carbon atoms and preferably containing from 5 to 16 carbon atoms.

Hydrophobic-treated pigments are described in particular in patent application EP-A-1 086 683.

For the purposes of the present patent application, the term "nacre" is intended to mean coloured particles of any form, which may or may not be iridescent, in particular produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye in particular of the abovementioned type, and also nacreous pigments based on bismuth oxychloride. They may also be mica particles, at the surface of which are superposed at least two successive layers of metal oxides and/or of organic dyestuffs.

The nacres may more particularly have a yellow, pink, red, bronze, orangey, brown, gold and/or coppery colour or tint.

As illustrations of nacres that may be introduced as interference pigments into the first composition, mention may be made of the gold-coloured nacres sold in particular by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown nacres sold in particular by the company Engelhard under the name Nu-antique copper 340XB (Cloisonne) and Brown CL4509 (Chromalite); the nacres with a copper tint sold in particular by the company Engelhard under the name Copper 340A (Timica); the nacres with a red tint sold in particular by the company Merck under the name Sienna fine (17386) (Colorona); the nacres with a yellow tint sold in particular by the company Engelhard under the name Yellow (4502) (Chromalite); the red nacres with a gold tint sold in particular by the company Engelhard under the name Sunstone G012 (Gemtone); the pink nacres sold in particular by the company Engelhard under the name Tan opale G005 (Gemtone); the black nacres with a gold tint sold in particular by the company Engelhard under the name Nu antique bronze 240 AB (Timica), the blue nacres sold in particular by the company Merck under the name Matte blue (17433) (Microna), the white nacres with a silvery tint sold in particular by the company Merck under the name Xirona Silver, and the golden-green pink-orange nacres sold in particular by the company Merck under the name Indian summer (Xirona), and mixtures thereof.

The composition according to the invention may also be free of dyestuffs.

Fillers

A cosmetic composition used according to the invention may also comprise at least one filler, of organic or mineral nature.

The term "filler" should be understood to mean colourless or white solid particles of any shape which are in a form that is insoluble and dispersed in the medium of the composition. These particles, of mineral or organic nature, can give body or rigidity to the composition and/or softness and uniformity to the makeup. They are different from dyestuffs.

Among the fillers that may be used in the compositions according to the invention, mention may be made of silica, kaolin, bentone, starch, lauroyllysine, and fumed silica particles, optionally hydrophilically or hydrophobically treated, and mixtures thereof.

A composition used according to the invention may comprise one or more fillers in a content ranging from 0.1% to 15% by weight relative to the total weight of the composition and in particular from 1% to 10% by weight relative to the total weight of the composition.

Preferably, a composition according to the invention comprises at least one compound chosen from fillers, waxes, pasty fatty substances, semi-crystalline polymers and/or lipophilic gelling agents, and mixtures thereof.

Usual Additional Cosmetic Ingredients

A composition used according to the invention may also comprise any usual cosmetic ingredient, which may be chosen especially from antioxidants, additional film-forming polymers (lipophilic or hydrophilic), fragrances, preserving agents, neutralizers, sunscreens, sweeteners, vitamins, free-radical scavengers and sequestrants, and mixtures thereof.

Needless to say, a person skilled in the art will take care to select the optional additional ingredients and/or the amount thereof such that the advantageous properties of the composition according to the invention are not, or are not substantially, adversely affected by the envisaged addition.

A composition according to the invention may more particularly be a composition for making up and/or caring for the lips.

A composition according to the invention may constitute a liquid lipstick, or a more or less thick cream or paste for the lips, such as a lip gloss or lip butter, for example.

The composition according to the invention may be manufactured via the known processes generally used in cosmetics or dermatology.

The composition according to the invention may be conditioned in any type of device that is common for fluid cosmetic compositions intended especially to be applied to the lips.

It may thus be envisaged to use devices containing a container comprising an applicator equipped with a ball (roll-on), a container of dispensing pen type, terminated with an end provided with at least one orifice through which the composition may be expelled, or alternatively terminated with a felt or with a flocked tip, or with a brush; a container comprising a dip applicator, for instance a brush.

Such devices may or may not be provided with a mechanism for dispensing the composition making it possible to expel the said composition from the container to the application member, or to the support. It should be noted that this mechanism may advantageously comprise a means for metering out the composition.

The examples that follow are presented as illustrations of the invention and cannot be interpreted as limiting its scope.

EXAMPLE

The following composition is prepared (the contents are expressed as weight percentages of active material, unless otherwise indicated):

| | |
|---|---|
| Cyclopentasiloxane (and) PEG/PPG-18/18 Dimethicone (dispersion at 12.5% by weight; Dow Corning 5225C Formulation Aid from the company Dow Corning) | 20* |
| Phenyl trimethicone (Dow Corning 556 Cosmetic Grade Fluid from the company Dow Corning) | 6 |
| Apricot kernel oil (*Prunus armeniaca* Kernel Oil; Apricot Kernel Oil from the company Desert Whale) | 5 |
| White petroleum jelly (Vaseline Blanche Codex 236 from the company Aiglon) | 4 |
| Disteardimonium hectorite (Bentone 38 VCG from the company Elementis) | 0.75 |
| Glycerol | 5 |
| Propylene glycol | 2 |
| Propylene carbonate | 0.07 |
| Preserving agent | 0.3 |
| Sequestrant | 0.05 |
| Water | qs 100 |

*content expressed as commercial product

Preparation Protocol:

The components of the oily phase are placed in a heating pan and the whole is brought to a temperature sufficient to melt the solid/pasty ingredients and to obtain a homogeneous mixture.

The components of the aqueous phase are then added with stirring (Rayneri) to obtain an inverse emulsion.

The deposit of the composition on the lips gives a uniform, thin, light, non-greasy and non-tacky deposit that dries quickly.

The state of the lips is improved, in particular their softness. This effect is persistent even after stopping the treatment.

The invention claimed is:

1. A water-in-oil emulsion cosmetic composition, comprising:
    from 15% to 55% by weight, relative to the weight of the composition, of an aqueous phase comprising one or more moisturizers or humectants,
    at least one silicon oil, and
    from 30% to 5% by weight relative to the weight of the composition of a lipophilic phase comprising:
        1 to 20% by weight relative to the weight of the composition of at least one polar non-volatile hydrocarbon-based first oil selected from the group consisting of a non-volatile ester oil, a fatty acid triglyceride which comprises from 7 to 40 carbon atoms and which is liquid at room temperature, a hydrocarbon-based plant oil, and a mixture thereof,
        from 8% to 30% by weight, relative to the weight of the composition, of at least one volatile or non-volatile, hydrocarbon-based or silicone apolar oil, from 0.15% to 20% by weight relative to the weight of the composition of at least one solid compound whose melting point is at least 30° C. and which is selected from the group consisting of a polar or apolar hydrocarbon-based compound, a wax and a pasty substance, and
        at least one emulsifying surfactant system,
    wherein the composition comprises at least one phenyl silicone oil, optionally bearing a dimethicone fragment and not more than 20% by weight of a lipophilic phase of a hydrocarbon-based apolar compound of synthetic origin.

2. The composition according to claim 1, comprising: at least one moisturizer or humectant selected from the group consisting of a polyhydric alcohol comprising from 2 to 6 hydroxyl radicals, a sugar, a urea and a derivative thereof, lactic acid and a salt thereof, hyaluronic acid and a salt thereof, an AHA, a BHA, sodium pidolate, serine, ectoin and a derivative thereof, chitosan and a derivative thereof, collagen, plankton, an extract of *Imperata cylindra*, an acrylic acid homopolymer, β-glucan, a mixture of passionflower oil, apricot oil, corn oil and rice bran oil, a C-glycoside derivative, a musk rose oil, an extract of the zinc-enriched microalga *Prophyridium cruentum*, arginine, or a mixture thereof.

3. The composition according to claim 1, which comprises not more than 10% by weight, relative to the weight of the composition, of the one or more moisturizers or humectants.

4. The composition according to claim 1, wherein the first oil is selected from the group consisting of:
- a monoester of formula $R_1COOR_2$ in which $R_1$ represents a linear or branched, saturated or unsaturated, or aromatic fatty acid residue comprising from 4 to 40 carbon atoms and $R_2$ represents a hydrocarbon-based chain containing from 4 to 40 carbon atoms, with the proviso that a sum of carbon atoms of radicals $R_1$ and $R_2$ is greater than or equal to 18,
- a fatty acid triglyceride, a caprylic/capric acid triglyceride and a mixture thereof, glyceryl triheptanoate, glyceryl trioctanoate or a $C_{18-36}$ acid triglyceride;
- a hydrocarbon-based plant oil, an unsaturated triglyceride, a liquid fraction of shea butter or a liquid fraction of cocoa butter, and
- a mixture thereof.

5. The composition according to claim 1, wherein the lipophilic phase comprises the non-volatile hydrocarbon-based or silicone apolar oil, which is selected from the group consisting of non-phenyl silicone oil; phenyl silicone oil optionally comprising a dimethicone fragment; a hydrocarbon-based oil or a derivative thereof, squalane, isoeicosane, naphthalene oil, a hydrogenated or non-hydrogenated polybutene, a hydrogenated or non-hydrogenated polyisobutene, a hydrogenated or non-hydrogenated polydecene; a decene/butene copolymer, a polybutene/polyisobutene copolymer; or a mixture thereof.

6. The composition according to claim 1, wherein the lipophilic phase comprises the volatile hydrocarbon-based or silicon apolar oil, which is a silicone oil, a hydrocarbon-based oil, a fluoro oil, or a mixture thereof.

7. The composition according to claim 1, wherein a content of the at least one volatile or non-volatile, hydrocarbon-based or silicone apolar oil ranges from 5% to 40% by weight relative to the weight of the composition.

8. The composition according to claim 1, which comprises one or more volatile silicone oils.

9. The composition according to claim 1, wherein the at least one solid compound has a melting point of from 30° C. to 100° C. and is selected from the group consisting of:
- a polar hydrocarbon-based compound;
- an apolar hydrocarbon-based compound;
- a polar hydrocarbon-based compound; and a mixture thereof.

10. The composition according to claim 1, wherein the at least one emulsifying surfactant system is selected from the group consisting of a fatty acid ester of a polyol; a silicone surfactant; and a polymer of a polyoxyalkylenated glycol fatty acid ester.

11. The composition according to claim 1, wherein the emulsifying surfactant system comprises at least one cosurfactant of a polyol alkyl ester.

12. The composition according to claim 1, wherein a content of the emulsifying surfactant system ranges from 1% to 6% by weight relative to the weight of the composition.

13. The composition according to claim 1, further comprising: at least one dyestuff.

14. The composition according to claim 13, wherein the at least one dyestuff is in a fluid form.

15. A process for treating a subject's lips, the processing comprising:
applying the composition according to claim 1 to the lips.

* * * * *

UNITED STATES PATENT AND TRADEMARK OFFICE
CERTIFICATE OF CORRECTION

PATENT NO. : 9,789,035 B2
APPLICATION NO. : 15/102468
DATED : October 17, 2017
INVENTOR(S) : Roshanak Debeaud et al.

Page 1 of 1

It is certified that error appears in the above-identified patent and that said Letters Patent is hereby corrected as shown below:

In the Claims

Column 28, Line 37, Claim 1, "30% to 5%" should read --30% to 85%--.

Signed and Sealed this
Tenth Day of December, 2019

Andrei Iancu
*Director of the United States Patent and Trademark Office*